United States Patent [19]
Wilson

[11] Patent Number: 5,850,630
[45] Date of Patent: *Dec. 15, 1998

[54] TOOL KIT WITH AUDIBLE PROMPTING FOR FIRST AID AND THE LIKE

[76] Inventor: J. Anthony Wilson, 650 Picacho La., Santa Barbara, Calif. 93108

[*] Notice: This patent issued on a continued prosecution application filed under 37 CFR 1.53(d), and is subject to the twenty year patent term provisions of 35 U.S.C. 154(a)(2).

[21] Appl. No.: 714,594

[22] Filed: Sep. 16, 1996

Related U.S. Application Data

[63] Continuation of Ser. No. 259,453, Jun. 13, 1994, abandoned.

[51] Int. Cl.[6] .......................................................... G10L 5/02
[52] U.S. Cl. ............................................. 704/270; 364/400
[58] Field of Search .................................... 395/2.79, 2.8, 395/2.83, 2.86; 206/803

[56] References Cited

U.S. PATENT DOCUMENTS

| | | | |
|---|---|---|---|
| 4,303,395 | 12/1981 | Bower | 434/226 |
| 4,513,866 | 4/1985 | Thomas | 206/570 |
| 5,086,391 | 2/1992 | Chambers | 364/413 |
| 5,521,812 | 5/1996 | Feder et al. | 364/400 |

*Primary Examiner*—David R. Hudspeth
*Assistant Examiner*—Harold Zintel
*Attorney, Agent, or Firm*—Michael G. Petit

[57] ABSTRACT

An instructional tool kit which includes a case having a lower section and a lid which can be clasped shut or opened to a convenient angle to expose the inside contents to user viewing. The lower section of the case is compartmentalized for storing selected tools and supplies. The upper section or lid consists of a speaker, a keypad, a light an optional video screen and various electronics including at least one digital signal processing chip. The keypad has a plurality of tasks indicated thereon, each key representing a different task. Upon pressing a key, the internal electronics addresses and plays a selected set of instructions through the speaker or displays the instructions on a video screen, enabling the user to select and apply the correct tool(s) to complete the task. Appropriate pauses, stops, skips, resumptions and instructions are built into the system to be entered by separate keys. The audible prompts, either with or without a video display, permit the user to perform emergency or other tasks without having to read instructions or otherwise be distracted. The kit of the present invention is particularly useful as a first aid kit.

7 Claims, 3 Drawing Sheets

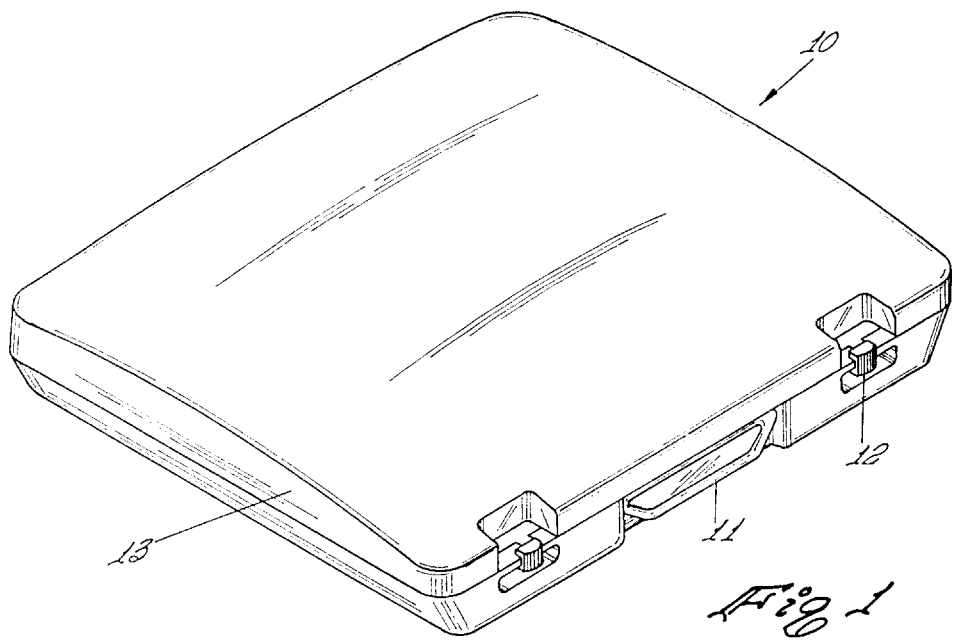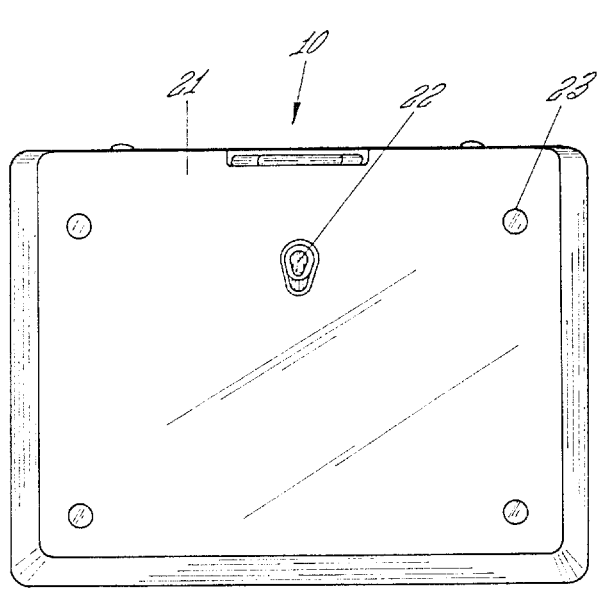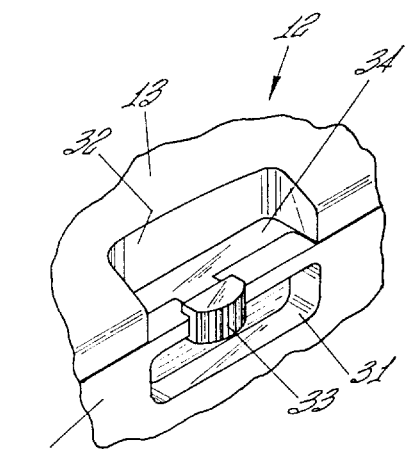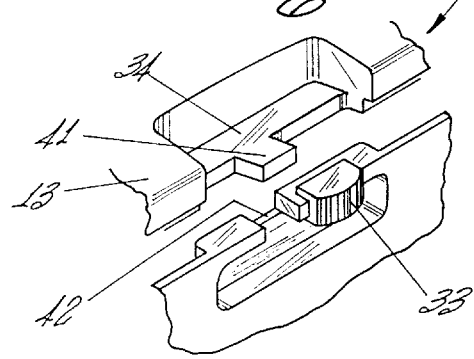

TOOL KIT WITH AUDIBLE PROMPTING FOR FIRST AID AND THE LIKE

CROSS REFERENCE TO RELATED APPLICATIONS

This is a continuation of application Ser. No. 08/259,453 filed Jun. 13, 1994, now abandoned.

BACKGROUND OF THE INVENTION

1. Field of the Invention

This invention relates to a tool kit having sensory instructional prompting to perform a task and more particularly to a first aid kit having audible and/or visual instructional prompts.

2. Prior Art

Anyone who has tried to assemble a child's bicycle the night before Christmas can readily appreciate the value of well-presented instructions for performing a particular task. Viewing a set of instructions, selecting a tool and/or parts to be assembled, and performing each of a sequence of tasks as illustrated in the instructions provides numerous distractions. This is particularly true if the task to be performed relates to a procedure associated with a life-or-death condition or just an anxiety-producing situation, such as when administering first aid.

For the critically ill or severely injured victim, the difference between life and death often depends upon the immediate institution of life-saving measures and treatment before transporting a victim to a hospital. The implementation of these life-saving measures often requires the use of specialized equipment. For a person who becomes seriously ill or injured away from a hospital, life-saving treatment requires such specialized equipment to be properly used; in many instances by a non-skilled individual.

One of the problems with prior art first aid kits is the inability to rapidly identify and access the emergency tools needed to perform a particular procedure. Presently designed kits carrying the specialized equipment may take the form of a conventional suitcase. When the case is opened, a variety of tools confronts the user. The selection of a particular tool from the millieu to perform a particular function requires some degree of focus and a clear analysis of the problem to be solved. That is, the person must pick the right tool for the right job and then use the tool appropriately.

Accordingly, it would be a significant advancement in the art to provide an emergency medical kit which carries most of the necessary medical equipment to provide first aid to a patient and which has an audible instructional prompt therein. Such a kit enables the user to identify a particular problem by pushing a button and have the tools needed to perform the necessary tasks to solve the problem identified for him. Such identification may include the location of the particular tool or tools. The instructions should further go on to inform the user of how to employ the tool(s) to perform the particular procedure. Such a kit is described hereinafter.

SUMMARY OF THE INVENTION

The present invention relates to a tool kit having a plurality of tools therewithin for performing a variety of tasks. Selector keys, which are used to identify a particular task, and the associated instructional prompting circuitry form one portion of the kit. The task to be performed is selected by pushing or depressing a selector key. Once the key is pressed, an audible and/or video signal is produced indicating the tools that are required to perform the task. A separate compartment of the kit contains a plurality of tools and forms another portion of the kit. In response to the audible prompt, the correct tools, which are clearly labeled to ease identification, are selected and removed for performing the task. The instruction then continues providing detailed step-by-step information directing how to perform that particular task with the tools at hand. The tool kit preferably has a light therewithin that illuminates the contents of the kit when the case is opened so that it may be used in the dark as, for example, during an earthquake or other emergency. The kit is preferably battery-powered.

It is an object of this invention to provide an instructional tool kit for performing a limited number of tasks using a variety of tools.

It is a further object of this invention to provide a kit for performing a limited number of tasks employing a variety of tools wherein the instructions for performing the task and for identifying and locating the particular tools needed to complete the task is an integral feature thereof.

It is a further object of this invention to provide a first aid kit having an audible instruction for performing a particular task.

It is still another object of the invention to provide a first aid kit which can be used by an individual speaking a language other than English.

It is yet another object of this invention to provide a tool kit for performing a variety of tasks wherein the instructions for performing the tasks using the tools within the kit are prerecorded on a memory.

It is still another object of this invention to be able to randomly select a set of instructions associated with performing a particular task from a preprogrammed memory.

It is still another object of this invention to provide a kit for performing a variety of tasks using a plurality of tools wherein the instructions are provided audibly and may be repeated as per a simple command.

These and other objects of the invention will soon become apparent as we turn now to a brief description of the drawings and a description of the preferred embodiments.

BRIEF DESCRIPTION OF THE DRAWINGS

FIG. 1 is a perspective view of a tool kit case in a closed position in accordance with the present invention.

FIG. 2 is a bottom view of a tool kit case in accordance with the present invention.

FIG. 3 is an enlarged view of the clasp mechanism for fastening the lid of the case according to the present invention.

FIG. 4 is an enlarged view showing further detail of the clasping mechanism of the case housing the kit of the present invention.

DESCRIPTION OF THE PREFERRED EMBODIMENTS

Figure 5:
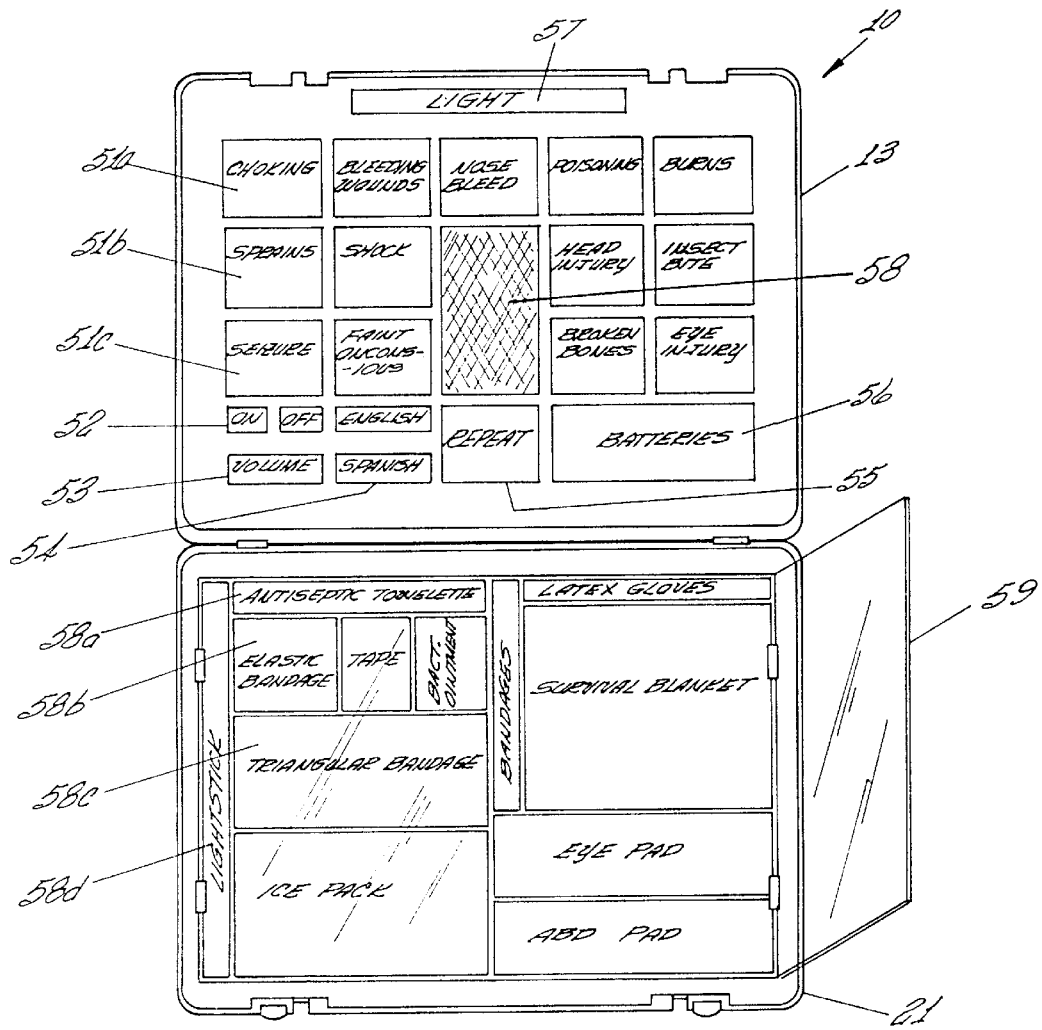
FIG. 5 is a top view of an opened first aid kit made in accordance with the present invention showing the keypad defining the tasks to be performed and the tools.

Voice synthesizers are well-known in the art. For example, Hutchins, in U.S. Pat. No. 4,583,524; the contents of which are incorporated herein by reference, describes a voice synthesizer having instructions for the performance of CPR. Hutchins' device employs read-only memory for storing instructions and a "CMOS" speech synthesizer chip for driving the audio amplifier which, in turn, drives a speaker to provide instructions to a person administering CPR. The instructions may be reset.

Another example of a speech synthesizer used to provide instructions is described in U.S. Pat. No. 5,008,942 to Kikuchi. The Kikuchi device monitors the status of a CAT-scan instrument and instructs the patient according to the condition of the instrument. Further examples of speech synthesis technology applicable for audible instructions are set forth in U.S. Pat. Nos. 5,030,101; 4,805,220; 4,669,121; and 4,970,673. In a speech synthesizing system a memory stores a plurality of instructions which are in the form of speech data and an address-designating circuit for designating an address of the memory. A synthesizer synthesizes a speech signal based on speech data from the memory in accordance with the synthesizing condition.

An instructional tool kit made in accordance with the present invention is indicated generally at the numeral 10 in FIG. 1. The kit 10 has an outer case with a top 13 and a bottom 21. A handle 11 is provided for convenience in carrying. A fastening mechanism 12 is also provided. Turning now to FIG. 2, the underside 21 of the kit 10 is shown. The outer surface of the bottom 21 of the kit 10 preferably has a hanging means 22 and/or a foot means 23 for storing the kit on a wall or on a horizontal surface such as a shelf or countertop, respectively.

In FIG. 3, an enlarged view of the latching mechanism 12 is shown. The latch 12 consists of a flat surface 34 projecting from the bottom of a recess 32 in the top or lid 13. The bottom 21 of the case has a recess 31 therein and a slide 33 mounted thereupon. In FIG. 4, the slide 33 is shown slid to the right to unlatch the case. A tab 41 on the top or lid 13 mates with a groove 42 in the base or the bottom 21 of the case. The tab 41, when placed into the slot 42 provides a locking mechanism for the case when the catch 33 is slid to the left.

FIG. 5 shows a first aid kit made in accordance with the present invention. The first aid kit 10 has a top portion 13 and a bottom portion 21. The inside of the top portion 13 has a keypad having a variety of task keys 51a, 51b, 51c, and so forth affixed thereto. Each of the task keys 51a–c indicate a particular medical emergency or problem. For example, 51a indicates choking, 51b indicates a sprain. Still other keys indicate other conditions such as insect bite, head injury, broken bone, and so forth. The inside of the top 13 of the case also includes a power source such as a battery pack 56 and electronics (not shown). A speaker means 58 provides an audible signal to the user. A light 57 goes on when the kit is opened, and/or the switch 52 is turned on. There is a volume adjust 53. There is preferably a switch means 54 for changing languages. A repeat button 55 enables the user to stop and repeat a particular instruction.

The bottom 21 of the case contains a variety of tools as are required for meeting the medical emergencies as defined by the task keys. A window 59, preferably hinged, covers the tools 58a, 58b, 58c, and so forth. The tools may include alcohol, iodine, a thermometer, elastic bandage, an icepack, a splint, and so forth. Depressing one of the task keys 51a–c activates a voice instruction indicating which tools to use for that particular condition. The voice instruction further goes on to instruct the user on how to use each particular tool to treat that particular emergency.

Figure 6:
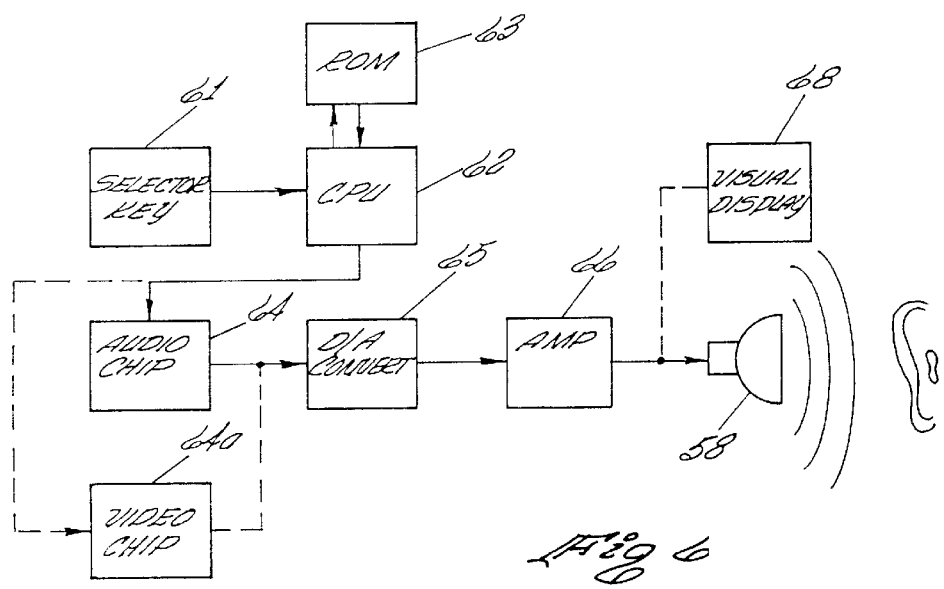
FIG. 6 is a generalized schematic diagram showing the arrangement of electronics for performing the audible or visual instruction accompanying each task.

In practice, the kit is opened and the light 57 goes on. The language default position may be preset to be English or Spanish or any other language by language selection means 54. The condition to be treated is selected and the task key 51 depressed. This depressed key indicates a task which identifies a message to be verbally transmitted to the user of the kit. Such a voice communication can be generally accomplished by means of a speech synthesizer as shown in FIG. 6. In FIG. 6, a memory 63 contains a set of instructions relating to each of the individual tasks 51. A selector key 61 is depressed to generate a signal indicating a particular task and an associated instructional message to be played. This signal is sent to a CPU which searches the memory 63 for the correct message and retrieves it and applies it to an audio chip 64 or a video chip 64a or both. The audio chip generates the appropriate audio signal from the digital message stored in memory. The audio signal goes through a digital-to-analog converter 65 and an amplifier 66 which drives a speaker 58 or a visual display 68. A repeat button 55 may be pressed to reset the message at the beginning.

Figure 7:
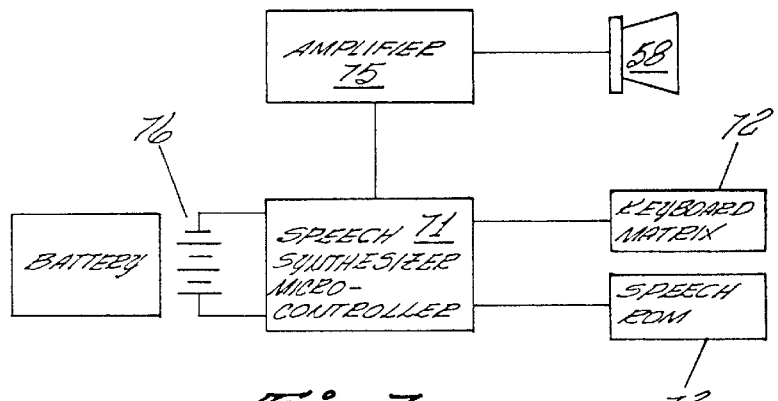
FIG. 7 is a schematic block diagram showing the arrangement of electronic components in a particularly preferred embodiment of the present invention.

A more detailed description of the electronics useful for providing instructions in accordance with the kit of the present invention is shown in FIG. 7. The heart of the synthesizer is a single chip 71 which incorporates an 8-bit microprocessor, a speech synthesizer, ROM, RAM and input/output ports. A suitable chip 71 is a TSP50C10 speech synthesizer made by Texas Instruments, Inc., 1001 E. Campbell Road, Richardson, Tex. 75081.

An input device such as a keyboard matrix 72 is suitable for identifying a particular message which is retrieved from the speech ROM 73. The speech ROM may also be incorporated into the chip 71. The TSP50C10 has an 8 K-Byte ROM and the TSP50C11 has a 16 K-Byte ROM. For many applications this internal memory is sufficient to store the required instructions. A TSP60C18 speech ROM may be used for additional memory. The audio signal is presented to a speaker 58 by means of an amplifier 75. A battery 76 is a suitable power source.

Figure 8:
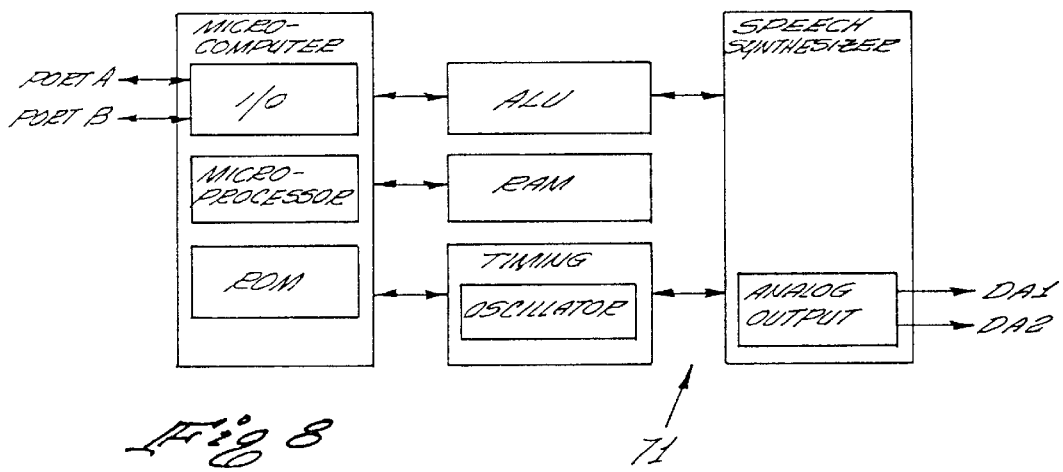
FIG. 8 is a schematic block diagram of the speech synthesizer microcontroller.
Figure 9:
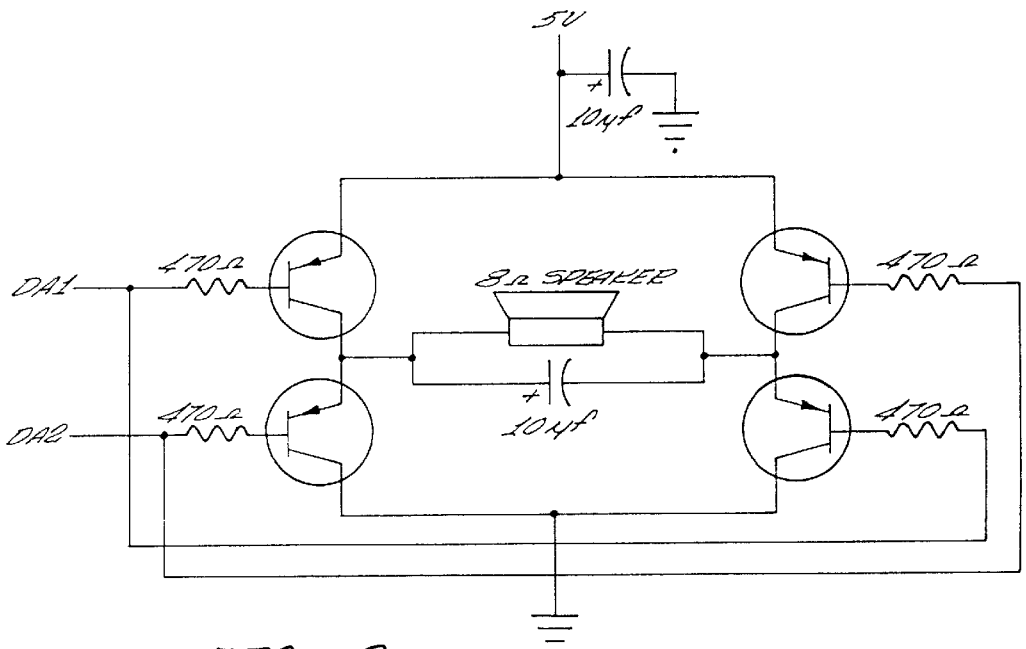
FIG. 9 shows an audio output circuit for use with the speech synthesizer microcontroller of the present invention.

A block diagram of the speech synthesizer and microprocessor chip is shown in FIG. 8. The chip can be divided into several functional blocks. The ALU (Arithmetic Logic Unit) and RAM are shared by the speech synthesizer and the microcomputer. The internal microprocessor fetches speech data from the internal or external ROM, decodes the speech data and sends the decoded data to the synthesizer. The microprocessor also smoothes the speech data between fetches. The output of the synthesizer can be used to drive either transistor or IC amplifiers such as is shown in FIG. 9.

While particular embodiments of the present invention have been illustrated and described, it would be obvious to those skilled in the art that various other changes and modifications can be made without departing from the spirit and scope of the invention. It is therefor, intended to cover in the impending claims all such changes and modifications that are within the scope of this invention.

What we claim is:

1. An instructional medical tool kit for use by user in carrying out a plurality of medical emergency related tasks, said instructional tool kit comprising:

Tools and supplies adapted for performance of each of said plurality of tasks;

instructional storage and playback electronic circuitry comprising: (a) a plurality of task selection keys, each task selection key being associated with a particular task selected from the said plurality of medical emergency related tasks and being adapted to permit the user to select the particular task from said plurality of tasks; (b) data storage means comprising a central processing unit and electronic memory adapted to store instructional data concerning each of said plurality of tasks and being selectable by said task selection keys, and audible play back means comprising audible instruction play back circuitry and a speaker adapted to audibly output said instructional data concerning said task selected by the user, a repeat key to allow a user to repeat a particular step in a selected task, and at least one of a language selection key and a volume key, and wherein each task comprising the plurality of tasks includes a plurality of steps, each step requiring the identification or use of at least one of said tools and supplies, and wherein upon activation of one of said task selection keys, said data instruction storage means will output to said audible playback means audible instructions to instruct user how to perform said selected task in a step-by-step manner; and (c) a case with a top portion and a bottom portion, wherein said tools and supplies are adapted to be contained in one of said top portions and bottom portions of the case, and the plurality of keys of said task selection means is located in the other of said top portion and bottom portion of the case and are disposed to be easily accessible when said case in an open position.

2. The instructional medical tool kit of claim 1 wherein said instructional storage and play back electronic circuitry further comprises visual display means adapted to visually display task data information selected by the user.

3. The instructional medical tool kit of claim 1 wherein said tools and supplies adapted for performance of each of said plurality of tasks are adapted to be contained in said bottom portion of said case and said plurality of task selection keys is located in said top portion and is adapted to be easily accessible when said case in an open position.

4. An instructional medical tool kit operable for enabling a user to perform a plurality of medical emergency related tasks, said instructional medical tool kit comprising:

(A) tools and supplies adapted for use in the performance of at least one of said plurality of tasks;

(B) a plurality of touch-activated task selection keys operable for sending a signal to a memory wherein the task selection keys permit a user to choose a particular task contained within said plurality of tasks, each task comprising said plurality of tasks further comprising at least one step requiring the identification or use of at least one of the said tools or supplies, and wherein the performance of all steps associated with said each task results in the performance of the selected task;

(C) a computer means having a programmable memory capable of receiving and sending a signal and operable for:
  (i) receiving a task selection signal from said task selection keys;
  (ii) identifying a particular task from among a plurality of tasks in response to receiving said signal from a task selection key;
  (iii) searching said programmable memory;
  (iv) selecting the appropriate step response corresponding to said task selection signal;
  (v) generating and sending task-related voice data to a playback means;

(D) playback means operable for receiving a signal communicating voice data from said computer means, the playback means adapted to provide audible instruction to a user corresponding to performing a particular step to accomplish the task selected by the user;

(E) a speaker device operable for providing audible instruction in response to receiving a signal from said playback means;

(F) a volume key operable for controlling the audio output amplitude of the speaker device;

(G) a touch-sensitive repeat key operable for sending a signal allowing a user to repeat an instruction corresponding to a particular step of a selected task;

(H) at least one language selection key; and (I) a case with a top portion and a bottom portion wherein said tools and supplies are adapted to be contained within one of said top portion or bottom portion of the case, and the plurality of keys of said task selection means are adapted to be located in the other of said top portion or bottom portion of the case, said task selection keys being disposed to be accessible when said case is in an open position.

5. The instructional medical tool kit of claim 4 wherein said tools and supplies are adapted to be contained in said bottom portion of said case and said plurality of keys of said task selection means is located in said top portion and is adapted to be easily accessible when said case is in an open position.

6. The instructional medical tool kit of claim 4 wherein said audible data includes video display data.

7. The instructional medical tool kit of claim 5 wherein said programmable memory further includes video display data.

* * * * *